United States Patent
Bakshi

(10) Patent No.: US 8,188,327 B1
(45) Date of Patent: May 29, 2012

(54) ISOOCTENE/ISOOCTANE PROCESS

(76) Inventor: Amarjit S. Bakshi, Houston, TX (US)

( * ) Notice: Subject to any disclaimer, the term of this patent is extended or adjusted under 35 U.S.C. 154(b) by 211 days.

(21) Appl. No.: 12/657,954

(22) Filed: Feb. 1, 2010

Related U.S. Application Data

(63) Continuation of application No. 11/454,044, filed on Jun. 15, 2006, now abandoned.

(51) Int. Cl.
*C07C 2/02* (2006.01)
*C07C 7/00* (2006.01)

(52) U.S. Cl. ........ 585/502; 585/255; 585/259; 585/263; 585/265; 585/277; 585/310; 585/329; 585/414; 585/510; 585/511; 585/514; 585/518; 585/519; 585/520; 585/639; 585/726; 585/809

(58) Field of Classification Search .................. 585/255, 585/259, 263, 265, 277, 310, 329, 414, 502, 585/510, 511, 514, 518, 519, 520, 639, 726, 585/809

See application file for complete search history.

(56) References Cited

U.S. PATENT DOCUMENTS

| | | | | |
|---|---|---|---|---|
| 5,994,601 A | * | 11/1999 | Nierlich et al. | 585/329 |
| 6,037,510 A | * | 3/2000 | Vicari et al. | 585/263 |
| 6,660,898 B1 | * | 12/2003 | Pyhalahti et al. | 585/510 |
| 7,273,957 B2 | * | 9/2007 | Bakshi et al. | 585/255 |
| 2008/0081939 A1 | * | 4/2008 | Bakshi | 585/809 |

* cited by examiner

*Primary Examiner* — Prem C Singh
(74) *Attorney, Agent, or Firm* — Richard L. Moseley

(57) ABSTRACT

This invention covers a process for dimerizing of isobutylene to Iso-octene and unique configuration is being disclosed, where the Feed is diluted to low level with recycle which has essentially no Iso-octene, dual catalyst system, new selectivator (IPA) and successive catalyst stages if needed to enhance the conversion. The process is very selective and provides higher isobutylene conversion.

Additionally the invention also covers the hydrogenation of olefins to Paraffin, Iso-octene to Iso-octane product under moderate conditions and with dual or single catalyst system.

4 Claims, 6 Drawing Sheets

RHT Iso-Octene Process

RHT Iso-Octene Process
Revamp of Reactive Distillation MTBE Unit

RHT Iso-octene to Iso-octane Hydro

ISOOCTENE/ISOOCTANE PROCESS

This is a continuation of application Ser. No. 11/454,044 filed Jun. 15, 2006 now abandoned.

FIELD OF THE INVENTION

The invention relates to producing dimer of Isobutylene especially but covers the dimerazation of Isoamylenes as well. The Isobutylene dimerization provides a dimer but some of the normal butylenes' react with iso-butylene to produces some of isomers of these dimers. This dimer which is di-isobutylene is called commonly as Iso-octene is high octane compound similar to MTBE but without the environmental problems of MTBE. The major problem is this product is essentially olefinic and when there are specification as regards to olefin than it will have to be hydrogenated to Isooctane. Most of the MTBE plants can be converted to Iso-octene with little investment but one needs some higher capital investment for hydrogenation of Is-octene to Iso-octane. Additional drawback is that the Isooctene yield compared to MTBE is reduced by about 70 percent. The art of this invention relates specifically to a new selectivator for the catalyst and also unique configuration so as to produce higher selectivity product and enhancing the yield as well. This will be explained fully in the Figures so as to make it more understandable to the individuals who are familiar with the art of catalytic reactions.

The invention also covers the hydrogenation of Iso-octene to Iso-octane (to 99% hydrogenation of olefins) in dual catalyst system at lower pressure than the competing technologies, reducing the cost.

BACKGROUND OF THE INVENTION

Low molecular weight unsymmetrical Ethers such as MTBE, ETBE are produced from iso-olefins and methanol/Ethanol reaction in the presence of acidic sulfonated ion exchange catalyst (e.g. Amberlyst 15 or 35 or equivalent) to produce ethers and are commonly added to the gasoline so as reduce the pollution due to better burning qualities of these Ethers and Lower vapor pressure as well, which provide good burning gasoline, due to additional oxygen added through alcohol, and the combustion products have reduced CO in the combustion products. As this addition of Ethers was mandated by the Clean Air act of 1990 by EPA. These ethers have much higher octane and lower RVP of the gasoline blend that reduces the VOC's in the atmosphere. Addition of these compounds works as diluent also, which in turn reduce the other components of the gasoline blend like benzene, aromatics and olefins. In recent years due leakage of MTBE from the gas stations storage tanks, some leaks from using it in water skies in lakes, and as solubility of the MTBE in water is high, it has created controversy as regards to suitability of the ethers in gasoline especially in USA. Some over 20 odd states in USA have banned Ether addition in gasoline, and other states might follow the trend, though it is still being used in RFG in some states in USA. In USA approximately 230,000 bbl/d of Ethers was being used in the gasoline, and if it is taken away as being suggested and is being forcasted, it will have at least about 70,000 bbl/d of shortfall of gasoline if Iso-octene is produced. Thus producing of Iso-octene via this route will be a low cost option. But if the Isobutylene can be alkylated with other normal olefins in the alkylation plant (which is normally being done for n-butenes if MTBE units are upstream) and lot of the Alkylation plants will have revamped any way. The product will be higher than the Ethers but of lower octane. But one should note that alkylate is one of the most desirable component of the gasoline pool with reasonable high octane, no aromatics and no sulfur. But the alkylation plants need much higher investment and some cases would make economic sense to produce Iso-octene and/or iso-octane via dimerization route and than if need be hydrogenating the product to reduce the olefin content, and it all depends on the economics of each plant and the specification and the complexity of the refinery which produces the gasoline components.

The invention is in the field of dimerization of isobutylene in the presence sulfonated resin catalyst (e.g. Amberlyst 15 or 35 or equivalent), together with an trifunctional catalyst which is essentially resin catalyst doped into palladium (two bed approach in the reactor) and a new selectivator for solvating the catalyst which is Isopropyl alcohol. The configuration is provided to dilute the isobutylene in the feed to 5% or less by unique configuration and recycle of Iso-propyl alcohol and dual bed catalyst provides selective conversion of Isobutylene to dimer (Iso-octene), essentially 10 to 20% of the 1-butene plus 2-butenes also goes in the reaction to form codimers. In the reaction some trimer is also formed with small amount of tetramer and also some C8 Ethers as will be shown in the reaction Chemistry section of this patent. The palladium-doped resin catalyst selectively hydrogenates the butadiene and also stabilizes the olefins, which provide the longer catalyst life, as it does not polymerize on the catalyst.

The present disclosure and the art describes a process for producing Iso-octene and Iso-octane by dimerizing the isobutylene in C4 stream in the fixed bed down flow reactor(s). In general, isobutylene dimerization process is done in the presence of similar acid catalysts that are used for etherification. We have selected a dual and different catalyst to do the dimerization to enhance the catalyst life. Essentially, the process uses an art of using a small amount of selectivator for solvating the catalyst that helps in the reactions sites to available for the reaction. The catalyst pore size and properties are selected for enhancing the catalyst activity/life. The special catalyst have been listed in the later process description and are claims of the process so as to make dual catalyst beds an art claimed by this process. together with the special selectivator/solvating agent.

The Hydrogenation is designed either to use dual catalyst system, Nickel and followed by Palladium in the finishing reactor (one can use either of the catalyst in both the reactors if so desired). Provision is there to use Palladium Platinum catalyst in the finishing Reactor as an extension of this invention.

SUMMARY OF THE INVENTION

The process in this art claims that if feed has small amount of propylene (1 to 3%) which will be converted to isopropyl alcohol with small amount of water and iso-octene produced in the reactor which is taken as a bottom product in the debutanizer column. The Isopropyl alcohol will be recycled back to the reactor so as to have low requirement of propylene in the feed, propylene can be reduced to about 0.5% in the Feed, based on the losses in the process. The process in this art requires that IPA (isopropyl alcohol) be about .0.5% to 3.0% by wt in the $C_4$ feed to the reactor.

The Feed is water washed to remove the basic compounds in the feed and metal impurities especially acetonitrile which is well known catalyst poison for the etherification ion exchange catalyst. After the water wash, the Feed with slight amount of propylene is heated to the reaction temperature and is mixed with stoichiometric amount of hydrogen to hydrogenate the butadiene, and mixing it with recycle stream before sending it to the reactor. The feed is reacted to hydrogenate the butadiene with trifunctional catalyst and also forms the dimer in the down flow fixed bed reactor in both beds of catalyst. The recycle stream of Isopropyl alcohol (IPA) and the unreacted isobutylene with other $C_4$ components in the feed are recycled to the reactor so as to have low concentration of isobutylene in the reactor. This provides low conversion per pass in the reactor and it helps in having better selectivity. The 6 figures are herewith attached to describe the different configurations to provide the best catalyst activity, yield and selectivity.

The Isobutyelene dimerizes and produces Iso-octene and also some side reactions takes place which produce the isomers of Iso-octene reacting with isobutylene and other straight chain olefins. The configurations, catalyst selection, operating conditions are chosen to give best results for selectivity and yield, together with enhancing the catalyst life. In the reaction some trimer and very small amount of tetramer are also formed, together with small amount of $C_8$ ethers.

Similar to the etherification process, once the reaction has taken place in the Fixed Bed Reactor or Reactors as shown in the Figures, the reactor effluent goes to the debutanizer column, where Iso-octene product is taken as bottom product and C4 non reactive stream is separated as overhead product. The selectivator (IPA) and non-reactive $C_4$ stream can be taken as sidedraw and $C_4$ stream without IPA can be taken overhead. The overhead stream is normally sent to battery limit or alkylation unit. An alternate of this is that one can take the Isooctane and IPA in the bottom and send these to another column (existing methanol or alcohol column) and separate the IPA overhead and recycled to the reactor and bottom is Iso-octene product, this is very convenient in the case of revamp of MTBE unit. In the existing MTBE unit, Methanol recovery column is available to do this separation. The Methanol extractor can be used for any other use to enhance the yield and catalyst life or is available as idle equipment. As RHT flow sheets, show that unreacted reactantants can be recycled from debutanizer with the selectivator, as a sidedraw, to a side reactor or bulk catalyst can be installed in the debutanizer as shown in the FIGS. 3 and 5, to enhance the conversion.

The advantages of the disclosed process are an art of improved catalyst system (dual catalyst beds Resin doped with palladium and resin catalyst Amberlyst 15 or 35 or equivalent), new process configuration, increased catalyst life due to selective hydrogenation butadiene and a new and improved selectivator IPA are at the heart of the process. Additionally it is much better option than the proprietary catalyst processes, which are expensive and use single source supplier, and provide lower conversion and selectivity (it as for MTBE). The RHT process has additional advantage of simple reactor design, no cumbersome catalyst loading requirements. The process has the advantage of changing the catalyst while the unit is in operation. The major breakthrough is that by recirculation of the some the side draw liquid the feed isobutylene concentration is brought into range of one third to one fifth of the virgin feed concentration by dilution, which provides low conversion per pass and high selectivity. The product is sent back to the same location from where the sided raw was taken out from column, so there is no effect on the debutanizer size. The reducing per pass conversion by dilution provides longer catalyst life and better yields and selectivity and new selectivator of Isopropyl Alcohol are the major claims and benefit of the process. As the boiling point difference of MTBE and Iso-octene are far apart (about 100 F), there is no problem in separation of C4's and the Iso-octene in the existing MTBE column if one returns the reactor effluent at the side draw location.

The invention covers the hydrogenation of iso-octene to iso-octane catalytically under milder conditions (lower pressure) and using a configuration which helps to enhance the hydrogenation due to dual catalyst system and is lower cost. The pressure and temperature in the reactor are in the range of 250 psig to 450 psig, (preferably closure to 250 psig) and temperatures are in the range of 200 to 500 F (preferably closure to 300 F) and hydrogen about 1.5 to 2.0 times the stoichiometric (closure to 1.30 times) are used in the process. The WHSV in the first reactor is in the range of 1 to 4 (preferably close to 2 to 3) and in the finishing reactor 3 to 6 (preferably closure to 4 to 5).

This unique feature will be apparent to one who is skilled in the art from the figures and claims and brief description of the figures.

BRIEF DESCRIPTION OF THE FIGURES

In FIG. 4 and FIG. 5, alcohol extractor is deleted, but to save capital cost and to enhance the catalyst life it can be converted to iso-octene reactor and is being claimed by this art and patent claim.

DETAILED DESCRIPTION OF THE INVENTION

Figure 1:
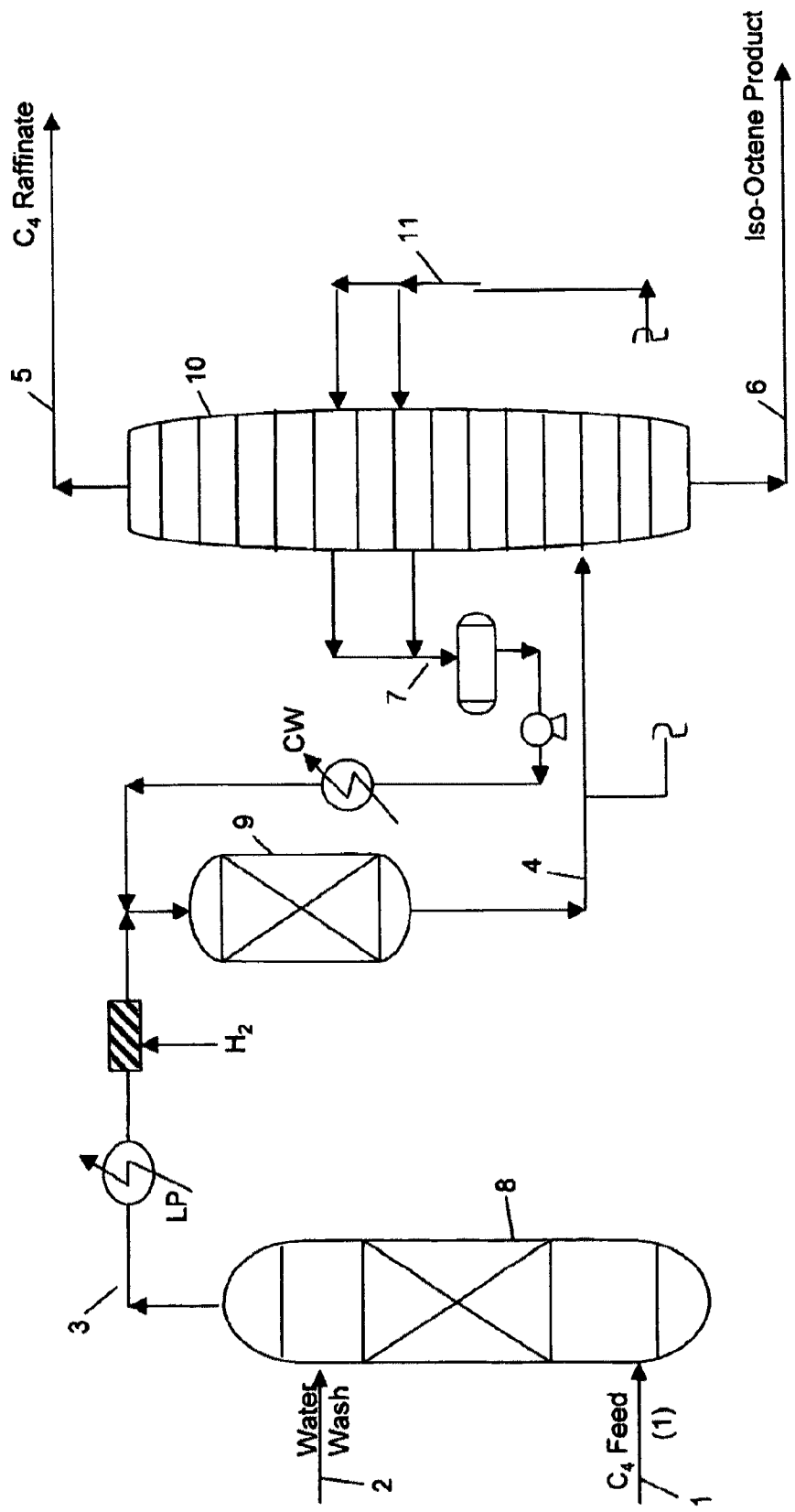
FIG. 1 is a simplified process flow diagram. The Feed stream 1 is washed in column 8 with water wash. The Feed stream 3 is heated to the reaction temperature and is mixed with hydrogen and is sent to the reactor item 9 which has dual catalyst. The feed to the reactor is mixed with as illustrated in the figure, with the selectivator and some of the side draw(s) or total draw(s) off stream 7, (which have some of unreacted isobutylene) taken from the debutanizer. This recycled stream to the reactor is provided so as to enhance the conversion, selectivity and product yield. The side draw quantity from the reactor is fed back to the column by stream 11 at the same location, hence this recycle products do not effect the column size. The recycled side draw streams to the reactor reduces the need for additional reactor and provides enhanced conversions and yields, and with proper design there is no effect on column and energy requirements. The $C_4$ are taken as stream 5 from the debutanizer item 10, and Iso-octene product is taken as stream 6. The reactor temperature is 100 to 120 F at the inlet and 140 to 150 F at the outlet of reactor and the pressure is kept at about 100 to 175 psig and it is essential that the reaction is done in liquid phase.

The major art and know how described here is a disclosure of producing Iso-octene by dimerizing isobutylene in the $C_4$ Stream from FCC, Steam Crackers, thermal crackers or on purpose dehydrogenation units. The reaction is performed in the presence of a new solvator/selectivator (IPA) which is helpful to keep the catalyst in solvated form, which stops the polymerization of olefins. The operating conditions and recycled streams are provided so that low conversion per pass is achieved due to dilution effect, and the total conversion of isobutylene is essentially kept to be optimum and is more than any other process. As reaction is pretty fast, one does not need too much of catalyst. The feed is washed for basic compounds that are poison for the catalyst similar to Etherification process. The present art provides a small amount of trifunctional catalyst so as to reduce any deactivation due to diolefins/butadiene. The dilution effect makes the process selective, due to low conversion per pass but the conversion is higher then the conventional processes on the fresh feed basis, the other straight chain olefins react to a lower degree with isobutylene under low per pass conversion, compared to other processes. The configuration provides reaction of the straight chain olefins lower compared to conventional scheme and the n-olefins are good feed stock for Alkylation. The codimers produced have lower octane than iso-octene. The catalyst used in this process is the same Ambrlyst 15, 35, 36 and CH10, K2431, K2621, K2629 or K2624 or equivalent. The resin catalyst doped with Pd (CH10 or K2624) or normal palladium or Nickel catalyst for hydrogenation is provided as dual layer bed, with WHSV with Pd doped catalyst. Pd or Nickel catalyst of 2 to 30, preferably in the range of 8 to 25 so as to selectively saturate the butadiene to olefin and also stabilize the olefins in the feed. As regards to other standard resin catalyst provided, WHSV is in the range 2 to 20, preferably in the range of 4 to 8.

The disclosed method and art can be understood by referring to the attached figures for the individuals who are familiar with the art, which are described in detail description of the figures herein. It should be understood that pipelines are in fact being designated when streams are identified and that stream are intended, if not stated when materials are mentioned. More over, flow control valves, temperature regulating and measuring devices, pumps, compressors, reboilers, condensers, coolers, heaters and drums and the like are understood as installed and operating in conventional relationships to the major items of equipment which are shown in the drawings and discussed hereinafter with reference to the continuously operating process of this invention and art there in. All of these valves, devices, pumps, and compressors, as well as heat exchangers, accumulators, condensers and the like are included in the term auxiliary equipment. It is also understood that any of the equipment or reactors can be decoupled by installing a drum in between two equipment items, so as to operate the these equipment at different conditions. It is an ability of ordinary skill in the art to implement such auxiliary equipment, as needed, in view of the present disclosure.

FIG. 1 illustrates an embodiment of the disclosure process. Iso-olefin Feed 1 should have small amount of propylene so as to make Isopropyl alcohol (IPA) which works as a Solvator/Selectivator. It is normal practice to wash the feed with water or run it through adsobsent where all the impurities are removed which deactivate the catalyst. After the water wash, $C_4$ Feed through line 3, is mixed with hydrogen before it is sent to stand alone reactor 9, if dual function catalyst is being used. Stand alone reactor 9 can be fixed bed down flow, or upflow reactor and could have a recycle with cooler if required. If one uses single function catalyst like Amberlyst 35, then no hydrogen feed is required. Effluent 4 from the reactor is fed to the column 10. Heavy components like Iso-octene together with some of the IPA goes to the bottom of the column and are taken as product through line 6. The Lighter components e.g. other $C_4$'s and unreacted isobutylene together with IPA goes in the top section of the column 10. Partial draw off or total draw off is taken from one or multiple places through line 7 and after cooling is fed the first reactor for additional conversion. So as to optimize the column size, reactor effluent is distributed in the same proportion as was put in through lines 4 sod 11. The dual function or single catalyst would be used so as to meet the catalyst life.

In the embodiment illustrated in the FIG. 1, reactants are exposed to the catalyst at low concentration due to recycle from the column, and in doing so the selectivity and conversion achieved are much better than the fresh Feed. If catalyst quantity provided is adequate to have WHSV of about 4 for the combined catalyst (dual function and single function) and the pressure and temperature are kept at 125 psig to 150 psig and temperature of 130 to 150 F is kept to provide optimum conversion and product quality. One has to see that minimum of 0.5 to 3% of IPA is in the reactor effluent which is being recycled with unconverted Feed through line 7. As shown in the FIG. 1 distillation is done to take the IPA with C4's in the draw off and that is being recycled. The non-reactive $C_4$ stream and normal olefins are taken overhead. In the normal feed very small amount of propylene in the Feed is required to make the additional IPA, which has been lost in the bottom and overhead streams.

Figure 2:
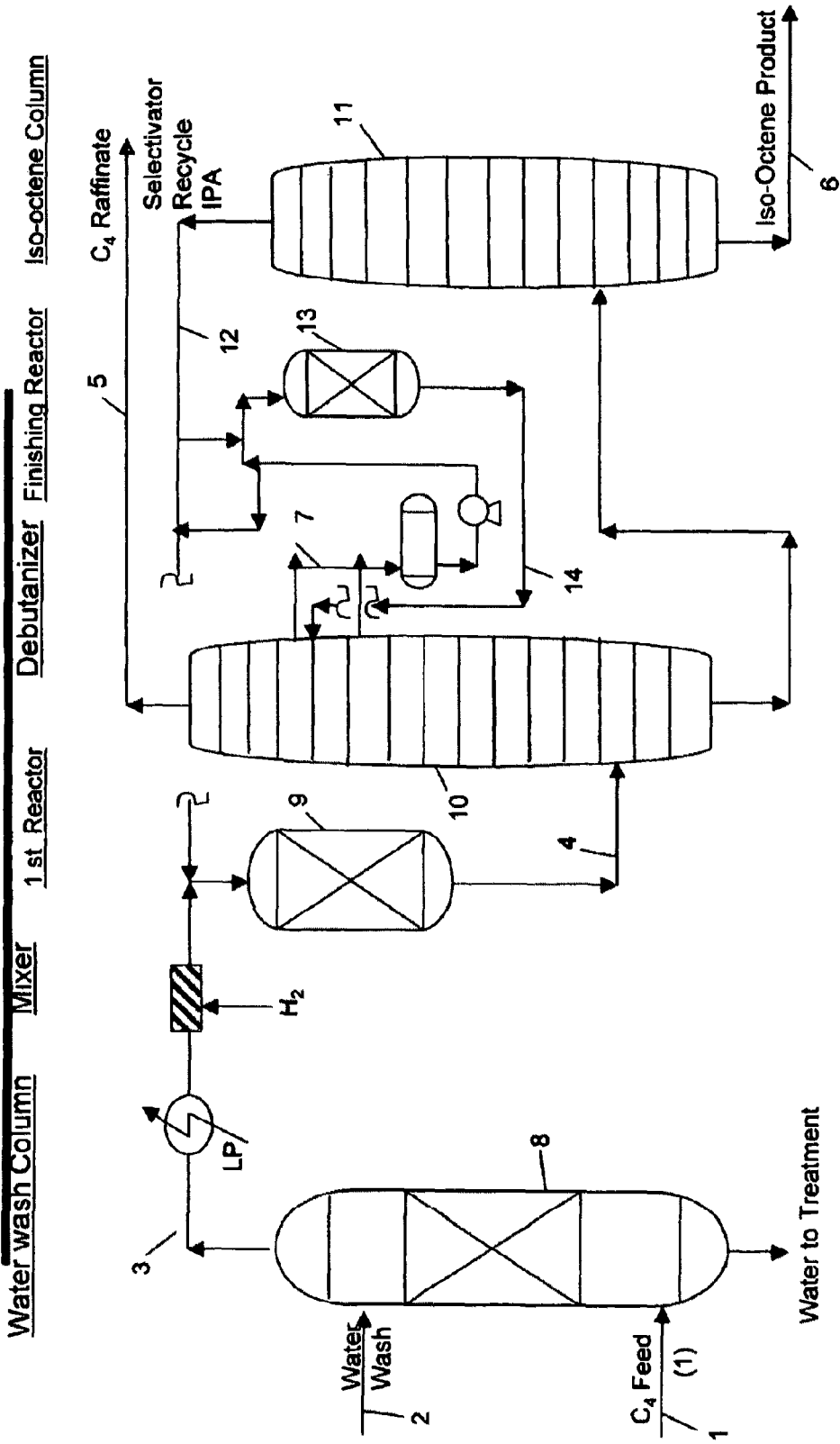
FIG. 2 is another mode of the simple process flow diagram where again Feed stream 1 is washed with water in column 8 and stream 3 after water wash is heated and mixed with hydrogen and is sent to the first Reactor item 9, which is mixed with stream 12 which is recycle IPA the selectivator and some of the draw off from stream 7. The Reactor effluent stream 4 is sent to debutanizer item 10 where $C_4$ and iso-octene is separated. Some of $C_4$ are taken as draw off from the debutanizer stream 7, which are recycled to first reactor and also to enhance the conversion are converted in the second Reactor Item 13 and the Reactor effluent stream a4 is sent back to the column for separation. The iso-octene together with IPA are sent to the column where IPA is taken overhead and is recycled to both the Reactors via stream 12 and the Iso-octene is taken as bottom product as stream 6 and is sent to OSBL or for hydrogenation to produce Iso-9octane as shown in FIG. 6. The configuration is similar to FIG. 1 except another reactor is added to enhance the conversion, selectivity and yield, (similar to FIG. 1), by taking a side draw(s) from the debutanizer and this stream is reacted in the side reactor in the presence of catalyst. The idea here is to do the reaction and conversion under controlled conditions so as to get the best yield and less catalyst deactivation. As in FIG. 1 the selectivator is distributed in both the reactors through stream 12. Additionally, the Iso-octene and the selectivator is taken in the second column overhead product and distributed into both the reactors. The $C_4$ stream is taken as overhead from the debutanizer column as stream 5 and is sent to alkylation or LPG system

FIG. 2 in this embodiment shows similar process flow diagram as FIG. 1, $C_4$ Feed is fed through line 1 and is washed in water wash Column (WWC). The $C_4$ Feed after washing, through line 3, is mixed with hydrogen before it is sent to stand alone reactor 9, if dual function catalyst is being used. Stand alone reactor 9 can be fixed bed down flow, or upflow reactor and could have a recycle with cooler if required. If one uses single function catalyst like Amberlyst 35, then no hydrogen feed is required. Effluent 4 from the reactor is fed to the column 10. Heavy components like Iso-octene together with of the IPA goes to the bottom of the column and is fed to the Iso-octene column where product Iso-octene is taken through line 6. The lighter components in debutanizer e.g other $C_4$'s and unreacted isobutylene is taken as overhead product, but some of the $C_4$'s are taken as side draw or multiple side draws through line 7 and are isobutylene is converted to Iso-octene in side reactor(s) 13. The reaction product from the side reactor is sent to the column where they have withdrawn from or some other location where concentration is similar, but without increasing the Column diameter or duties. As shown that IPA is taken overhead in Iso-octene Column 11 as overhead product and is recycled to both the reactor s first reactor 9 and the sidedraw reactor 13. The dual function or single catalyst would be used so as to meet the catalyst life and is the claim of the invention. The operating pressure, temperature is in the same range as mentioned in FIG. 1 above.

Figure 3:
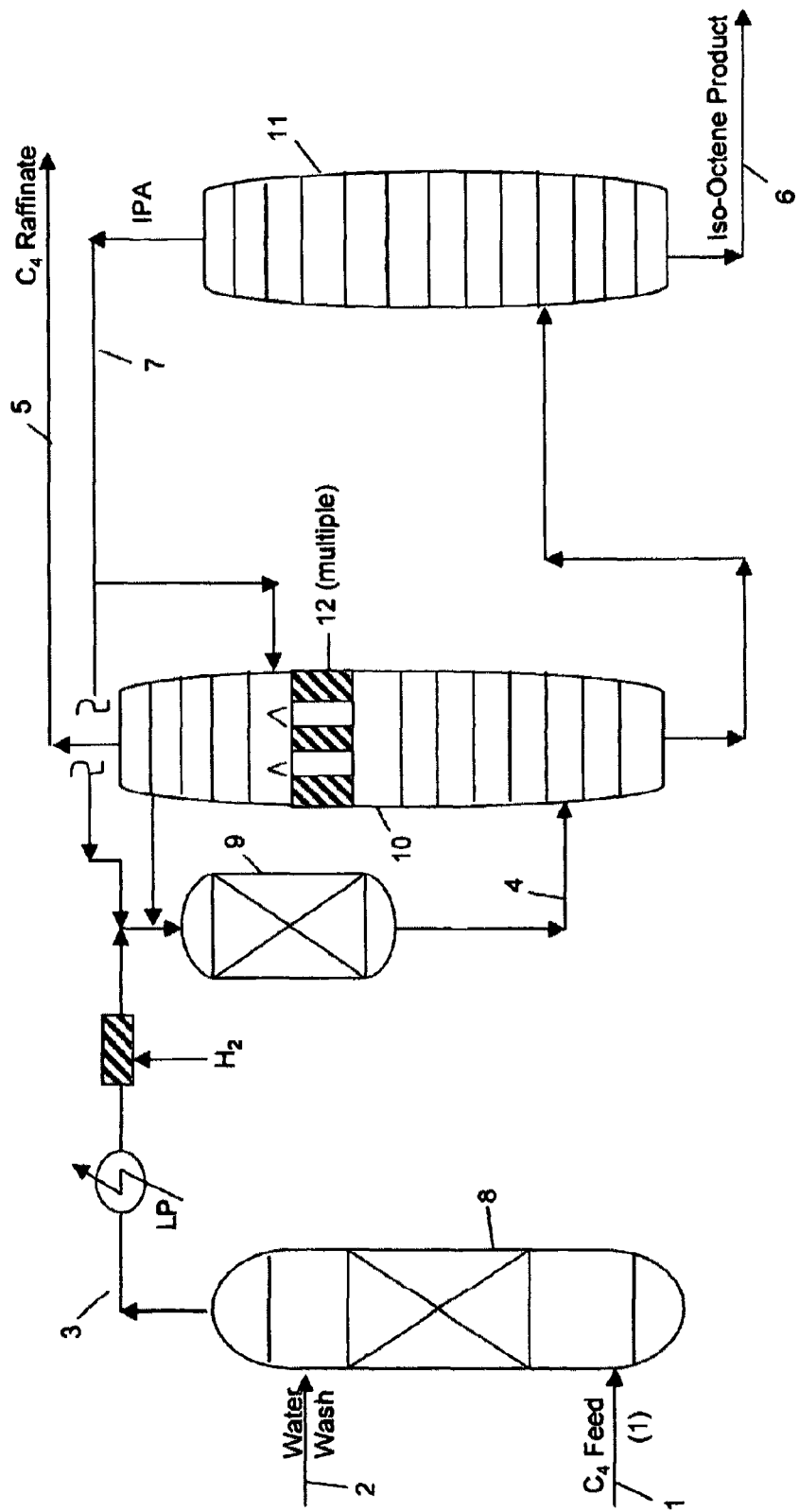
FIG. 3 is another mode of configuration to enhance the yield and conversion and selectivity and most of the elements are similar to FIG. 1 up to the first Reactor and the backend after the debutanizer. The first reactor does the reaction same as in FIG. 1, there is always IPA selectivator used in all the configurations shown in all the Figures. To enhance the conversion bulk catalyst can be installed in the debutanizer item 12, so that the reflux liquid is converted to iso-octene, and the vapor is bypassed through the chimney trays. This bulk catalyst is installed on the Johnson Screen grid and hold down plate is used to keep the catalyst in the debtanizer The design provides pressure balance in the chimney tray/trays by restricting the chimney flow so that slight liquid head is provided so as liquid to go through the catalyst in downflow manner as is the case normally. This restriction in chimney tray of the special nature is being claimed by the art of this invention. There could be multiple beds in the column but the bed height required is very small compared to the reactive distillation application. This is bulk catalyst, so the cost of catalyst is very low and is easy to install. Essentially the FIG. 3 configuration is similar to FIG. 1 except installing the bulk catalyst in the column. All the reaction is done in liquid phase. The Reactors, which use boiling in the reactor, are not efficient as some of the reactants go in vapor and the catalyst utilization is not optimum . . . .

FIG. 3 is another variation of FIGS. 1 and 2, $C_4$ Feed is fed through line 1 and is washed in water wash Column (WWC). The $C_4$ Feed after washing, through line 3, is mixed with hydrogen before it is sent to stand alone reactor 9, if dual function catalyst is being used. Stand alone reactor 9 can be fixed bed down flow, or upflow reactor and could have a recycle with cooler if required. If one uses single function catalyst like Amberlyst 35, then no hydrogen feed is required. Effluent 4 from the reactor is fed to the column 10. Heavy components like Iso-octene together with the IPA goes to the bottom of the column and is fed to the Iso-Octene column where product Iso-octene is taken through line 6. The lighter components in debutanizer e.g. other $C_4$'s and unreacted isobutylene are taken as overhead product. With the reflux some of isobutylene is reacted in the column bulk catalyst shown as 12 (can have multiple beds). IPA is taken as overhead product in Iso-octene Column 11, where IPA is recycled to the first stand alone reactor 9 and also to Column bulk catalyst section 12. These details of operating conditions and WHSV will be illustrated in a separate section. The debutanizer catalyst 12 is provided as bulk catalyst on the grating and Johnson screen is used to see that catalyst does not pass through to bottom of the column. The catalyst in the column enhances the conversion. Instead of bulk catalyst one can provide side reactor the other conditions remain the same as for FIGS. 1 and 2.

Figure 4:
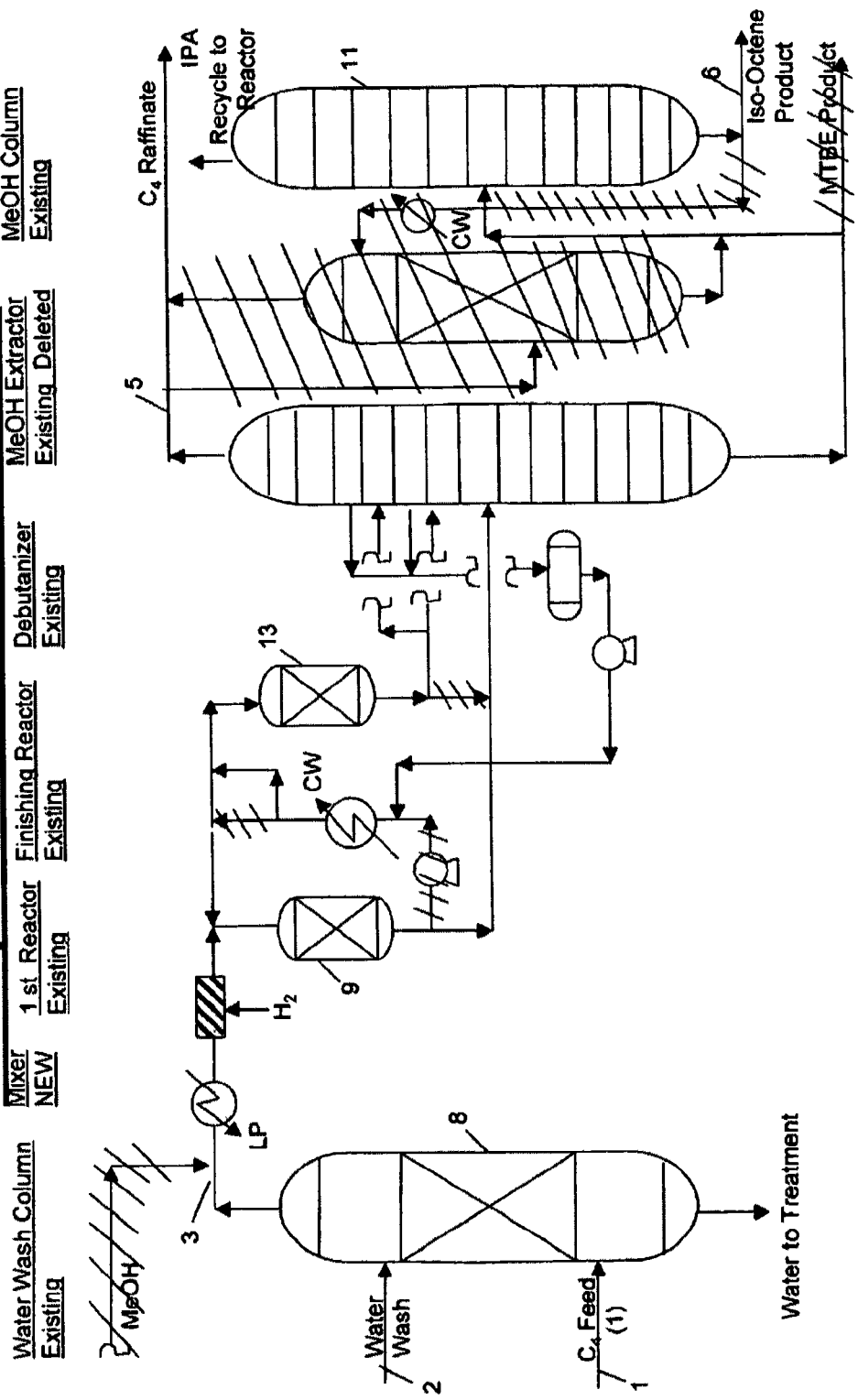
FIG. 4 is a MTBE unit process flow diagram, which is being converted to Iso-Octene process. The process flow diagram modification for revamp have been shown how to modify so as to be similar to FIG. 2, but it can be modified to be FIG. 1 or 3 easily if so required (based on the requirements of the process) to enhance the conversion and economics and capital investment requirements.

FIG. 4 is an embodiment in which it is shown how to revamp the existing MTBE unit. The hatched lines and equipment are to be deleted. Additional reactor in parallel may be required but might not be necessary. So most of the equipment is available and some piping modifications might be necessary. It is possible that all the instruments are adequate. So revamp cost are very low. Operating conditions and catalyst requirements are as for FIGS. 1, 2 and 3. In FIG. 4, $C_4$ Feed is fed through line 1 and is washed in water wash Column (WWC). The $C_4$ Feed after washing, through line 3, is mixed with hydrogen before it is sent to stand alone reactor 9, if dual function catalyst is being used. Stand alone reactor 9 can be fixed bed down flow, or upflow reactor and could have a recycle with cooler if required. If one uses single function catalyst like Amberlyst 35, then no hydrogen feed is required. Effluent 4 from the reactor is fed to the column 10. Heavy components like Iso-octene together with of the IPA goes to the bottom of the column and is fed to the Existing Methanol recovery column (Iso-octene column) where product Iso-octene is taken through line 6. The lighter components in debutanizer e.g. other $C_4$,s and unreacted isobutylene is taken as overhead product through line 5, but some of the $C_4$,s are taken as side draw or multiple side draws through line 12 and isobutylene is converted to Iso-octene in side reactor(s) 13 which is existing finishing MTBE reactor but has to be repiped. The reaction product from the side reactor is sent to the column where they have withdrawn from or some other location where concentration is similar, but without increasing the Column diameter or duties. As shown that IPA is taken overhead in Iso-octene Column 11 as overhead product through line 7, and is recycled to both the reactors, first reactor 9 and the side draw reactor 13 through line 14. The dual function or single catalyst would be used so as to meet the catalyst life and is the claim of the invention. The operating pressure, temperature is in the same range as mentioned in FIG. 1 above. Naturally the Methanol feed system and the methanol Extractor 15 can be used for alternate use in the unit to enhance yield and catalyst life.

Figure 5:
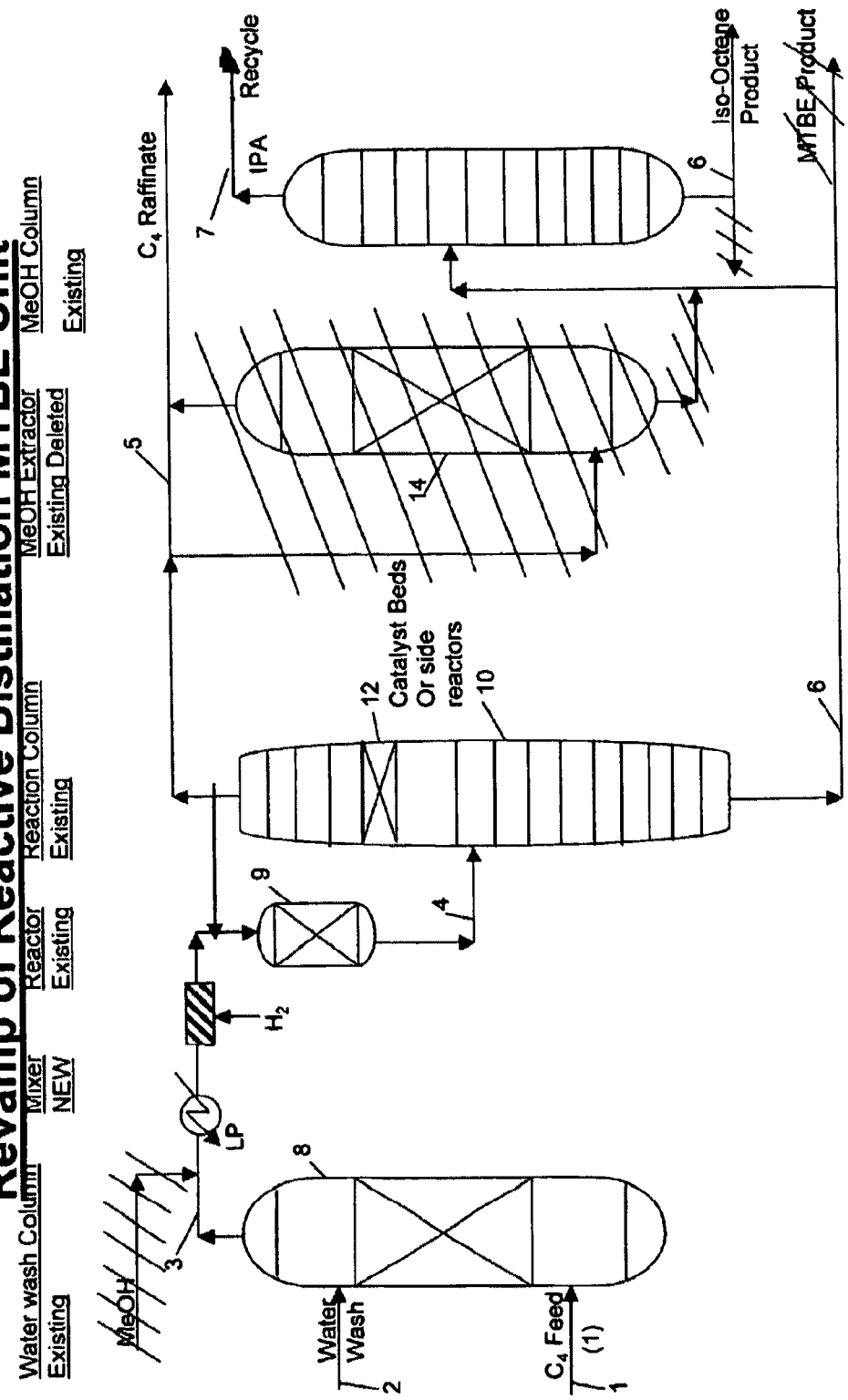
FIG. 5 is the similar process flow diagram to FIGS. 1 to 4, which covers all the options. This FIG. 5 includes recycling the Feed to first reactor, and having bulk catalyst item 12 installed in the debutanizer column together with revamping of the Reactive distillation column of MTBE unit at low cost, having a higher conversions, better selectivity and catalyst life.
Figure 6:
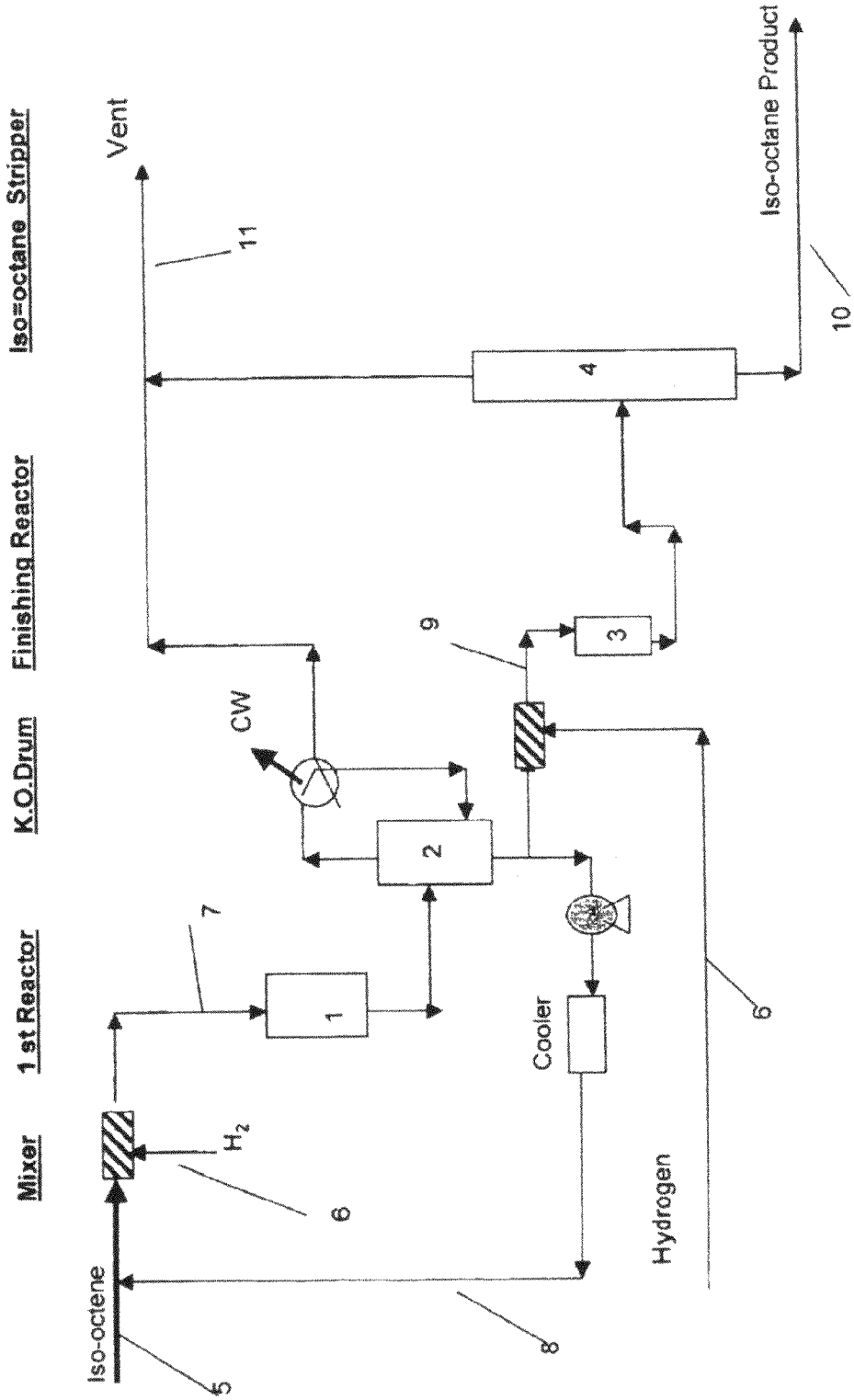
FIG. 6 is the hydrogenation of iso-octene to iso-octane. The Iso-octene from the OSBL or directly from the debutanizer is pumped through line 5 to the reactor pressure, it is mixed with the recycle stream 8 which provides the dilution and heat sink, mixed with hydrogen which is fed through line 6 and all are mixed by the inline Mixer before feeding to the Hydrogenation Reactor through line 7 at the reaction temperature and pressure. The Reactor product is flashed in Drum item 2, hydrocarbon vapor are condensed and sent back to drum. The vent is sent to fuel gas system. The Liquid from item 2 is fed to the Finishing Reactor item 3, after mixing with hydrogen by the inline Mixer. The Reactor effluent is fed to the Iso-octane Stripper item 4, to stabilize it. The Iso-octane product is taken as bottom product and cooled before sending it to storage.

FIG. 5 is illustrates an embodiment in which it is shown how to revamp the Reactive distillation MTBE unit to Iso-octene unit. The hatched lines and equipment are to be deleted. Additional reactor in parallel may be required but might not be necessary. So most of the equipment is available and some piping modifications might be necessary. It is possible that all the instruments are adequate. So revamp cost are very low. Operating conditions and catalyst requirements are similar to as for FIGS. 1, 2 and 3. In FIG. 4, $C_4$ Feed is fed through line 1 and is washed in water wash Column (WWC). The $C_4$ Feed after washing, through line 3, is mixed with hydrogen before it is sent to stand alone reactor 9, if dual function catalyst is being used. Stand alone reactor 9 can be fixed bed down flow, or upflow reactor and could have a recycle with cooler if required. If one uses single function catalyst like Amberlyst 35, then no hydrogen feed is required. Reactor effluent through line 4 is fed to the column 10. Heavy components like Iso-octene together with of the IPA goes to the bottom of the column and is fed to the Existing Methanol recovery column (Iso-octene column) where product Iso-octene is taken through line 6. The lighter components in debutanizer e.g. other $C_4$'s and unreacted isobutylene is taken as overhead product through line 5, but some of the $C_4$'s are taken as side draw or multiple side draws (not shown) and are recycled to the first reactor to reduce the conversion per pass, enhancing isobutylene conversion to Iso-octene in side reactor 9 which is existing first MTBE reactor but has to be repiped. The reflux in the column can be converted by installing bulk catalyst in the column as suggested in FIG. 3 or can be repiped as side reactors as shown in FIG. 2. Reaction product from the side reactor is sent to the column where they have withdrawn from or some other location where concentration is similar, but without increasing the Column diameter or duties. As shown that IPA is taken overhead in Iso-otene Column 11 as overhead product through line 7 and is recycled to both the reactor s first reactor 9 and the side Draw reactors through line 15 and some to the bulk catalyst in the column, reaction zone if required, though this might not be required. The dual function or single function catalyst would be used so as to enhance the catalyst life and is one of the claims of the invention. The operating pressure, temperature is in the same range as mentioned in FIG. 1 above. Naturally the Methanol feed system and the methanol Extractor 14, can be used for alternate use in the unit to enhance yield and catalyst life.

Individuals familiar with the skill in the art do understand the importance of removing the basic compounds by Feed water wash system. After water wash, the second major art in Iso-octene Technology is to have), 0.05 to 2.5% of Solvator/selectivator in catalyst (alcohol) with the Feed to provide good catalyst life and low polymerization. Here selectivator being used is Isopropyl Alcohol, and any other compound if they are boiling in that range will also recycle which can not be helped. The third art in this embodiment is being used is to have tri-functional catalyst at a very high WHSV (15 to 25), so as to see that the diolefins do not polymerize on catalyst. The other major art in the embodiment is reduce the conversion per pass in the reactor, which enhances the catalyst life and selectivity. The art has already been described so as to be able to use the existing column size by putting the recycle stream flows to at the same location from where these were so that there is no effect on debutanizer design compared to conventional processes. As $C_4$ and $C_8$ separation is pretty easy there is no problem in achieving this concept. The last but not the least is the selection of right catalyst and we will here suggest catalyst, which we claim, will provide optimum conversion and yield.

One of the major skill in the art is to have the clean feed devoid of basic compounds, right catalyst selection, selectivator and per pass conversion to be reduced. The process is for dimerizing the Isobutylene, but it also reacts with some straight chain olefins, which provides isomers with slightly lower octane. The reaction products are sent to the debutanizer where Iso-octane is separated from $C_4$ stream. Iso octene with other byproducts is sent to existing Methanol recovery column or new column to separate the selectivator and recycle it to the reactor. The bottom product is Iso octene with very good octane and can be hydrogenated to provide Iso-octane, which will provide the product, which will reduce the olefins, concentration in the gasoline pool.

All the figures show that unreacted feed can be recycled to the first reactor and isobutylene there in would be converted. to iso-octene or codimers. It will be diluted as well so the conversion per pass will go down and quality will be good. No doubt the selectivatir will be recycled either from this debutanizer or after separating in a second column. The other Option is by putting the side reactors conversion can be enhanced, but the recycle to the first reactor be still kept so as to have low per pass conversion, this is one of the major claim of the process. The column size will not be effected, as the products will be fed at the same location from where they are withdrawn. $C_4$ and iso-octene separations not difficult so there is no problem in separation and keeping the per pass conversion low in the reactor which provides better selectivity and catalyst life as well.

Alternatively, the catalyst can be installed in the column as bulk catalyst on a grating with Johnson Screen and a holddown grid, with chimneys for by passing the vapor. There could be more than single bed (multiple beds) and similarly the side reactor can be more than one to enhance the conversion, only major requirement is to keep the conversion low in the reactors and that enough selectivator is there so as to provide the catalyst solvated. Reactions stages can be as desired but normally in this application, two reaction stages will provide the economical conversion of about 95 to 99 wt % isobutylene.

In this patent, selectivator/solvator which is being used is Isopropyl Alcohol and any other compounds which boil at the same or close boiling compounds will automatically go with IPA and will be recycled to the reactor. The single pass conversion is to kept low so as to get the best selectivity.

The reaction is done around 100 degrees F. to 160 degrees F. and the reactor pressures are kept at around 95 to 150 psig. The catalyst used is Amberlyst CH10 (palladium or Nickel catalyst for selective hydrogenation, plus Amberlyst 35 or 36, or one can use Lewatit K 2624 plus K 2431 or SP112-H or equivalent Catalyst in resin family or zeolyte family but not limited to these catalyst or any catalyst which provides acidity for the reaction and the proper properties is acceptable and will be used. The dual catalyst system is claimed by the art in this process as selective hydrogenation is mandatory for the process to enhance the catalyst life, but if one is prepare to sacrifice the catalyst, than one can operate the unit without selective hydrogenation.

Examples of suitable selectivator/solvators could be any alcohol which boils below the Iso-octene so that it can be recycled to the reactor. Here RHT process has come up with an IPA selectivator, which is formed by hydration of propylene in Feed and small quantity of water, which are normally available in the feed with the same resin or acidic catalyst.

The first reactor operates at about 95 to 175 psig and 100 degrees F. to 190 degrees F. in the presence of above mentioned catalyst, together with selectivator and dilution so as to reduce the per pass conversion. The iso-olefin (isobutylene) in the Feed can be say from 7% to 60 percent in the $C_4$ feed stream. The high concentration feeds need careful consideration but the advantages is that some of these Feeds don't have basic compounds and also other olefins are in small quantity so the catalyst life and selectivity can be maintained if heat of reaction or per pass reaction is properly controlled.

95 to 99 wt % isobutylene conversions can be easily achieved with a reasonably high Octane product. The selectivity can be kept good so that boiling range of the product is similar to the gasoline boiling range. It is expected that 97 to 99 percent isobutylene is converted, and normal butylenes are converted from 10 to 25%. The product is expected to be about 80 to 90% C8 olefins and 10 to 20% of C12 Olefins with 0.1 to 1.0% of C16 olefins. But selectivity is much better than most of the processes available in the market due to reduced per pass conversion and lower temperature. Higher temperature and vapor in the reactor provides lower selectivity and conversion so reactor is operated in liquid phase as desired by the reaction kinetics.

In the embodiment of this patent, art is illustrated that one can get high conversions with one reactor, side reactors, by installing catalyst in the column, and there are advantages of each configuration to keep the conversion low by diluting the feed with recycle which provides high selectivity. For the most of cases, where this application will be applied be first to the existing MTBE units after that one will consider the on purpose MTBE merchant units and there is real advantage in realizing this once the MTBE is phased out. As shown in the FIGS. 4 and 5, RHT process with very little additional Capital cost can revamp the conventional or reactive distillation MTBE units.

The major invention in this embodiment is that using the IPA selectivator, Dual catalyst to stabilize the feed and reduce the butadiene by selective hydrogenation of the feed, provide dilution to reduce the conversion per pass which improves the selectivity and catalyst life and reduces the exotherm in the reactor, provide side reactors to enhance the conversion or by installing bulk catalyst in the column by providing vapor bypass of the bed with chimney trays. These are the major claims of this invention for producing Iso-octene.

EXAMPLES

The following example illustrates the feeds which could be used for making Iso-octene. These could be from multiple sources FCC $C_4$ Stream, Steam Cracker $C_4$ Stream and on purpose Isobutane Dehydrogenation units, which can provide good feed for Iso-octene production. The higher concentration feeds need is well suited to this configuration.

$C_4$ Feed from the FCC Unit:

| Component | wt % |
|---|---|
| Propane | 1.2 |
| Propylene | 0.7 |
| Isobutane | 23.9 |
| Isobutylene | 17.8 |
| 1-Butene | 13.7 |
| c-2-butene | 12.6 |
| t-2-butene | 14.3 |
| n-butane | 15.3 |
| $C_5$'s | 0.5 |
| Total | 100.00 |

Iso-octene Product

| | |
|---|---|
| $C_8$ olefins | 90 to 92% |
| $C_{12}$ Olefins | 7.5 to 9.0% |
| Other byproducts | 0.5 to 2.0% |

Iso-octane Product

| | |
|---|---|
| $C_8$ Paraffins | 91 to 93% |
| $C_{12}$ Paraffins | 7 to 8.5% |
| Other impurities | 0.5 to 2.0% |

The following reaction conditions and yields can be expected from this unit:
Based on the configuration and feed compositions following conditions will be required for the first and Side reactors configuration:
Inlet Temp (F) 100 to 180 (100 to 130 F preferable)
Pressure (psig) 100 to 175
LHSV $(hr)^{-1}$ 3 to 6
Iso-olefin Conversion (%) 97 to 99% (overall)
n-olefin Conversion: Minimize the olefin conversion to Codimers Reaction Chemistry
Iso-octane Reactions:

| | |
|---|---|
| 2 Isobutylene | Iso-octene |
| .Isobutylene + n-butykene | Codimers |
| Isobutylene + iso-octene | $C_{12}$ olefins |
| Iso-octene + Iso-octene | $C_{16}$ olefins |
| Alcohol + olefins | $C_8$ Ethers |

Iso-octane Reactions:

| | |
|---|---|
| $C_8$ olefins + $H_2$ | $C_8$ Paraffin |
| $C_{12}$ olefins + $H_2$ | $C_{12}$ Paraffin |
| $C_{16}$ olefins + $H_2$ | $C_{16}$ Paraffin |

The invention claimed is:

1. A process for the production of iso-octene from isobutylene contained within an FCC product stream, a thermal cracker product stream or a dehydrogenation product stream, said stream also containing water, propylene, dienes and unreactive $C_4$'s, comprising the steps of:
   (a) feeding hydrogen and said FCC product stream, a thermal cracker product stream or dehydrogenation product stream, down flow to a reactor containing a top bed of selective hydrogenation catalyst and a bottom bed of sulfonated resin catalyst;
   (b) selectively hydrogenating the dienes in said top bed;
   (c) dimerizing a portion of the isobutylene to iso-octene and hydrating a portion of the propylene with water to form isopropyl alcohol in said bottom bed;
   (d) removing an effluent from the bottom of said reactor, said effluent containing iso-octene, isopropyl alcohol, unreacted isobutylene and unreactive $C_4$,s;
   (e) feeding the effluent to a distillation column reactor wherein di-isobutene is taken as a bottoms product and isopropyl alcohol, unreacted isobutylene and unreactive $C_4$'s are taken as overheads or as side draws from designated trays;
   (f) recycling a portion of said side draws containing unreacted isobutylene, isopropyl alcohol and unreactive $C_4$'s to the top of said reactor in such quantities so as to reduce the isobutylene content in the feed to the reactor to 20 to 50 percent of the isobutylene contained within said FCC product stream, thermal cracker product stream or dehydrogenation product stream;
   (g) feeding a portion of said side draws to a second reactor containing a sulfonated resin catalyst to convert additional isobutylene to iso-octene; and
   (h) feeding the effluent from said second reactor to said distillation column reactor to the same tray from which it was removed.

2. The process according to claim 1 wherein the top bed of said reactor contains a tri-functional catalyst comprising a sulfonated resin catalyst doped with palladium.

3. The process according to claim 1 wherein said FCC product stream, thermal cracker product stream or dehydrogenation product stream also contains isoamylene and said isoamylene is dimerized in said bottom bed to produce di-isoamylene.

4. The process according to claim 1 wherein at least a portion of said iso-octene product is fed to a reactor containing a hydrogenation catalyst where a iso-octene is converted to iso-octane.

* * * * *